United States Patent [19]

Nicolau et al.

[11] Patent Number: 4,716,114

[45] Date of Patent: Dec. 29, 1987

[54] **PROCEDURE FOR THE ENHANCEMENT OF THE RESISTANCE TO ARSENITE AND ARSENATE OF *THIOBACILLUS FERROOXIDANS* AND *BACILLUS SUBTILIS***

[75] Inventors: Claude Nicolau, La Chapelle Saint Mesmin; Jacques Raimond, ST Jean la Ruelle, both of France

[73] Assignee: Inverko Industrie Vertriebs Kontor GmbH & Co., KG, Fed. Rep. of Germany

[21] Appl. No.: 719,337

[22] Filed: Apr. 3, 1985

Related U.S. Application Data

[63] Continuation-in-part of Ser. No. 496,390, May 20, 1983, abandoned.

[30] Foreign Application Priority Data

May 24, 1982 [DE] Fed. Rep. of Germany ....... 3219440

[51] Int. Cl.$^4$ .............................................. C12N 15/00
[52] U.S. Cl. .................................. 435/172.3; 935/38; 935/54; 935/56; 935/72; 935/74; 435/172.1; 435/172.2
[58] Field of Search ..................... 435/253, 262, 172.3; 935/14, 29, 52, 54, 56, 59, 72, 74, 38; 423/23, 87, 17; 75/118 R

[56] References Cited

U.S. PATENT DOCUMENTS

4,394,448  7/1983  Szoka et al. ...................... 435/172.3

OTHER PUBLICATIONS

Silver et al (1981), Journal of Bacteriology, vol. 146, No. 3, pp. 983–996.
Luong et al (1981), Proceedings of the 32nd Alaska Science Conference, University of Alaska Campus, Fairbanks, Alaska, pp. 48–49.
Tuovinen et al (1973), Archives of Microbiology, vol. 88, pp. 285–298.
Chang et al (1979), Molecular General Genetics, vol. 168, pp. 111, 115.
Sene et al in "Liposomes, Drugs and Immunocopetent Cell Functions", Academic Press, London (1981), pp. 67–79.
Boseeker et al (1978) Process Biochemistry.
Mao et al (1980) FEMS Microbiology, vol. 8, pp. 121–125.
Martin et al (1981), Canadian Journal of Microbiology, vol. 27, pp. 850–853.
Curtin (1983), Biotechnology (May) pp. 230–235.

*Primary Examiner*—Sam Rosen
*Assistant Examiner*—William J. Herald
*Attorney, Agent, or Firm*—Harness, Dickey & Pierce

[57] ABSTRACT

A process for increasing the resistance of *Thiobacillus ferrooxidans* and *Bacillus subtilis* to As (III) and As (V) by plasmid transformation.

6 Claims, 3 Drawing Figures

PROCEDURE FOR THE ENHANCEMENT OF THE RESISTANCE TO ARSENITE AND ARSENATE OF *THIOBACILLUS FERROOXIDANS* AND *BACILLUS SUBTILIS*

CROSS-REFERENCE TO RELATED APPLICATION

This application is a continuation-in-part of our application entitled "Procedure For The Enhancement Of The Resistance To Arsenite And Arsenate Of *Thiobacillus-Ferroxidans*," Ser. No. 496,390, filed May 20, 1983, now abandoned the disclosure of which is herein incorporated by reference.

BACKGROUND OF THE INVENTION

The present invention relates to a process designed to increase the resistance of bacterial strains, in particular *Thiobocillus ferrooxidans*, to As(III) and As(V), and also the bacteria thereby obtained and their application in particular in the extraction of gold from arsenopyrite deposits.

*Thiobacillus ferrooxidans* bacteria are the main microorganisms which leach metal sulfides: pyrites and CuS, for example, and also uranium ores. They are autotrophic bacteria when they grow in the presence of $Fe^{2+}$ ions and heterotrophic when they grow on an organic medium (for example glucose). There are already a few industrial installations which carry out this technique of bacterial leaching, chiefly for copper (USA) and uranium (South Africa, Canada).

The industrial techniques for leaching uranium have as their object the conversion of the uranium, which is present in ores in the form of insoluble oxide, to water-soluble uranium salt. The uranium core frequently contains pyrite ($FeS_2$) and the action of *Thiobacillus ferrooxidans* takes the effect in the following manner:

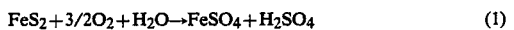

$$FeS_2 + 3/2O_2 + H_2O \rightarrow FeSO_4 + H_2SO_4 \quad (1)$$

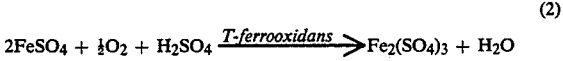

$$2FeSO_4 + \tfrac{1}{2}O_2 + H_2SO_4 \xrightarrow{T.\text{-}ferrooxidans} Fe_2(SO_4)_3 + H_2O \quad (2)$$

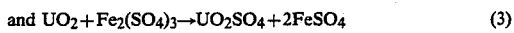

$$\text{and } UO_2 + Fe_2(SO_4)_3 \rightarrow UO_2SO_4 + 2FeSO_4 \quad (3)$$

$UO_2SO_4$ is soluble in water.

Since the oxidation of U(IV) to U(IV) is faster in the presence of the bacteria than in the presence of $Fe^{3+}$ ions alone, recent studies suggest that there is a direct action of *Thiobacillus ferrooxidans* on U(IV):

$$2UO_2 + O_2 + 2H_2SO_4 \rightarrow 2UO_2SO_4 + 2H_2O \quad (4)$$

Using the oxidizing capacities of this bacterium, 85% of the uranium in a low-grade ore (200 to 300 ppm of uranium) can be leached in 20 weeks. If the ore is more finely ground (particle size: 0.8 to 1.2 mm), in 9 weeks 60 to 70% of the uranium can be leached by the bacteria.

The reaction (2) is the basis of the process for bacterial leaching of uranium.

*Thiobacillus ferrooxidans* can also be used in order to extract gold from arsenopyrite deposits. The autotrophic bacterium digests the arsenopyrite and enables the metal to be extracted without having to roast the ore.

Unfortunately, the majority of strains of *Thiobacillus ferrooxidans* are very sensitive to As(III) and As(V) toxicity.

SUMMARY OF THE INVENTION

The present invention proposes to overcome this disadvantage by means of a process designed to increase the resistance of a bacterial strain to As(III) and As(V), characterized in that the said strain, which may or may not be resistant to As(III) and As(V), is transformed by plasmids carrying the genes which code for resistance to As(III) and As(V) and the elements which provide for their expression in the said bacterium.

It was in fact demonstrated that resistance to As(III) and As(V) was encoded by genes carried which were of plasmid origin, and that the transformation of bacterial strains by these plasmids endowed them with a resistance to As(III) and AS(V) when they were devoid of such resistance, and increased their resistance to AS(III) and AS(V) when the strains in question already possessed some degree of resistance to AS(III) and AS(V).

Quite unexpectedly, it was demonstrated that transformation of a strain of *T. ferrooxidans* resistant to As(III) and AS(V) by all of the plasmid DNA of this same strain increased very significantly the resistance of the transformant relative to the original strain.

DETAILED DESCRIPTION OF THE PREFERRED EMBODIMENTS OF THE INVENTION

Figure 1:
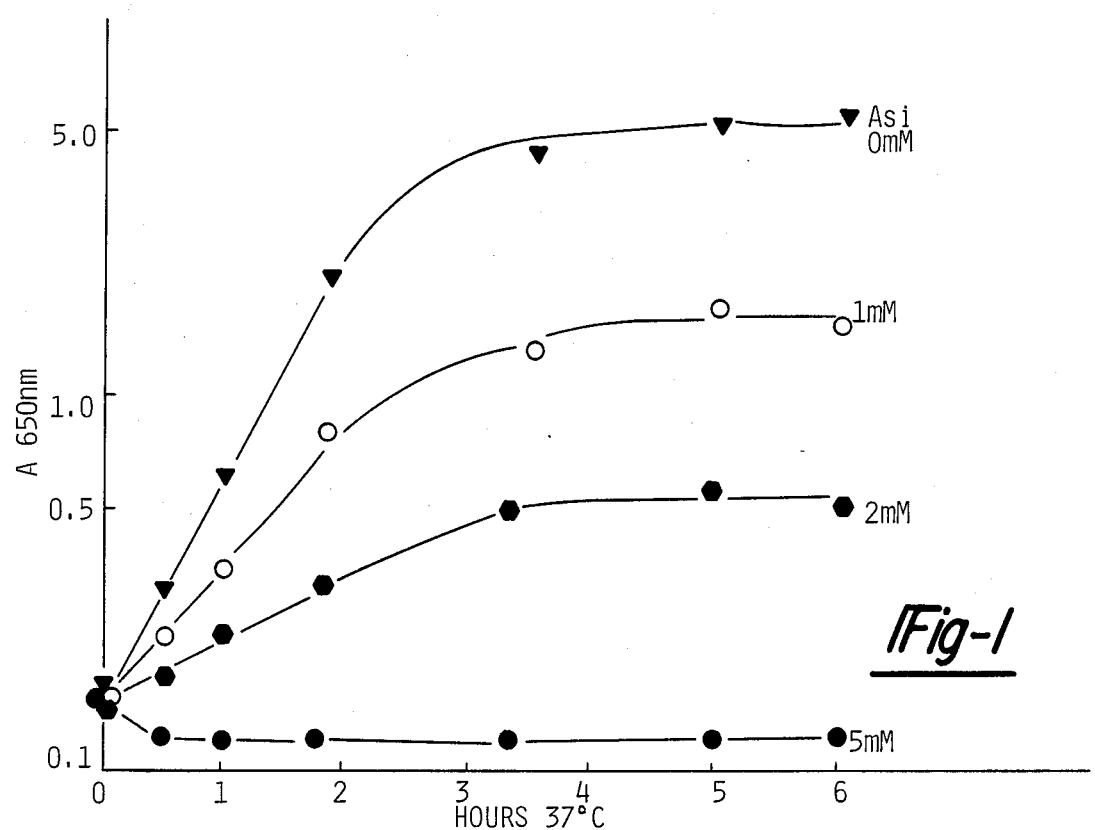

The transformation of the bacterial strain can be performed by any one of the techniques known in the field of genetic engineering, in particular, according to the size of the plasmid or plasmids used for the transformation. Thus, for large plasmids, the technique using liposomes will preferably be employed. In this process, protoplasts of the bacteria to be transformed are incubated with liposomes incorporating the said plasmids, and then the cell wall is regenerated after incubation.

The plasmids which can be used in this process are preferably extracted from a bacterial strain especially of *T. ferrooxidans* resistant to As(III) and AS(V), and are used as such, but they can also be partially synthetic.

Taking into account what was stated in the introduction, it will naturally be preferred to transform strains of Thiobacillus, and of *T. ferrooxidans* in particular, but, as will be shown, it is possible to transform other bacteria such as *Bacillus subtilis* and to endow them with resistance to AS(III) and As(V).

*Thiobacillus ferrooxidans* transformed according to the present invention is especially applicable to the leaching of metal ores, and especially arsenopyrite ores containing gold.

The microorganisms used can obtain highly varied plasmid profiles, and these microorganisms can thus contain, for example, the plasmids described in French Pat. No. A-81/16232 of 25.8.1981, namely pTL 12 (T. Tanaka and N. Kawano "Gene" Vol. 10, 1980, pages 131–136) and pHV 23 (B. Michel, E. Palka, B. Niaudet, S. D. Ehrlich "Gene" Vol. 12, 1980, pages 147–154), pBP1 (modified pTL12), pBP 2 (modified pHV 23).

Further characteristics and advantages of the present invention will emerge from the examples which follow.

Strains and culture conditions

*Thiobacillus ferrooxidans* strain Tf80 was obtained from the Laboratories of General Mining, Johannesburg, R.S.A. It is resistant to 6 mM sodium arsenite. The strain is cultured in the liquid medium defined by Tuovinen (7) to which there is added 3 mM sodium arsenite. The pH is adjusted to 1.5. 20 liters of culture are produced in a glass cylinder, with agitation and aeration. The temperature is maintained at 28°–30° C. The cells are harvested when 50% of the $Fe^{2+}$ is oxidized to $Fe^{3+}$. *Bacillus subtilis* is cultivated in liquid medium LB (6) except when special media are required for the transformation.

Preparation of plasmids from *Thiobacillus ferrooxidans*

The experimental design developed in the Laboratory for *Thiobacillus ferrooxidans* is adapted from various sources (3–6) (Tf 29, Tf 33, Tf35, Tf 80).

The cells harvested by centrifugation are washed with twice 50 ml of saline culture medium. The pellet, approximately 4 ml, is resuspended in 40 ml of SET (sucrose 25%, Tris 50 mM, EDTA 2 mM, pH 8). This suspension is frozen for 90 minutes at $-80°$ C. and then rapidly thawed and heated to 37° C. There are then added 8 ml of pronase predigested in TE buffer (20 mg/ml of Tris 10 mM, EDTA 1 mM, pH 1.4 incubated for 60 minutes at 37° C.).

This mixture, incubated for 5 minutes at 37° C., is rapidly cooled to 0° C., and 3.6 ml of 10% strength sodium dodecyl sulphate are added. After the mixture has been left standing for 30 minutes in an ice bath, 28 ml of 3M potassium acetate are added and the mixture is vigorously agitated for 10 minutes at 0° C., and then centrifuged for 30 minutes at 19,000 g (Sorvall Rotor GSA). To the measured supernatent two volumes of ethanol are added, and the solution is maintained for 15 minutes at 0° C. The precipitated DNA is harvested by centrifugation (5 min., 19,000 g). The DNA pellet is dissolved in 5 ml of TBS buffer (Tris 50 mM, NaCl 150 mM, pH 7.5), reprecipitated with 10 ml of ethanol, maintained for 5 minutes at room temperature and harvested by centrifugation for 10 minutes at 12,000 g (Sorvall Rotor SS34). The dried pellet, resuspended in TE, is analyzed by performing a cesium chloride gradient in the presence of ethidium bromide (40 h, 44000 rpm, Beckman Rotor 70 TI). The extracted, purified band is analyzed by elecgtrophoresis in 0.6% agarose gel at 30 volts for 18 hours in TEB buffer (Tris 18 mM, EDTA 0.5 mM, boric acid 18 mM, pH 8.25).

Preparation and transformation of *Bacillus subtilis* protoplasts

*Bacillus subtilis* 168 (G. Rapoport et al, "Molec. Gen. Genet" 176, 239–245, 1979) is used as receptor strain. The protoplasts are prepared and transformed according to the procedure of Chang and Cohen (8). The transformed protoplasts are incubated 90 minutes at 37° C. in the recommended expression medium, and then 90 minutes at 37° C. in the same medium to which 0.2 mM sodium arsenite has been added.

The protoplasts thus treated are plated on the solid regeneration medium as described by the authors but with 5 mM of sodium arsenite added to select the transformants. After 48 to 72 hours of incubation at 37° C., colonies develop at the surface.

A control transformation is carried out by transferring to the initial strain plasmid pC 194, which endows the strain with resistance to chloramphenicol.

EXAMPLE 1

Transformation of *Bacillus subtilis*

1.1. The plasmid profile of strain Tf 80 of *Thiobacillus ferroxidans* obtained on argarose gel shows several bands, but it is not known which of these confers the resistance to arsenite.

Before attempting to transfer this character to strain 168 of *Bacillus subtilis*, chosen for its capacity readily to yield protoplasts having a high efficiency of transformation of plasmids (8), the effect of sodium aresenite on this strain was studied.

1.2. The growth of *Bacillus subtilis* 168 in the presence of sodium arsenite is studied. *Bacillus subtilis* 168 is cultured overnight in LB medium.

The culture is diluted twenty-fold in fresh medium to which sodium arsenite has been added at the concentrations shown. The cultures are incubated at 37° C. with agitation and growth is followed by measuring the absorbance at 650 nm. The results obtained are shown in FIG. 1.

The curves in FIG. 1 show that the growth of *Bacillus subtilis* 168 is limited by sodium arsenite at concentrations of 1 and 2 mM. The doubling time of 30 minutes, which characterizes the strain in the medium in question at 37° C., increases to 50 minutes and 110 minutes, respectively. In the presence of 5 mM arsenite, growth is immediately and permanently inhibited.

Figure 2:
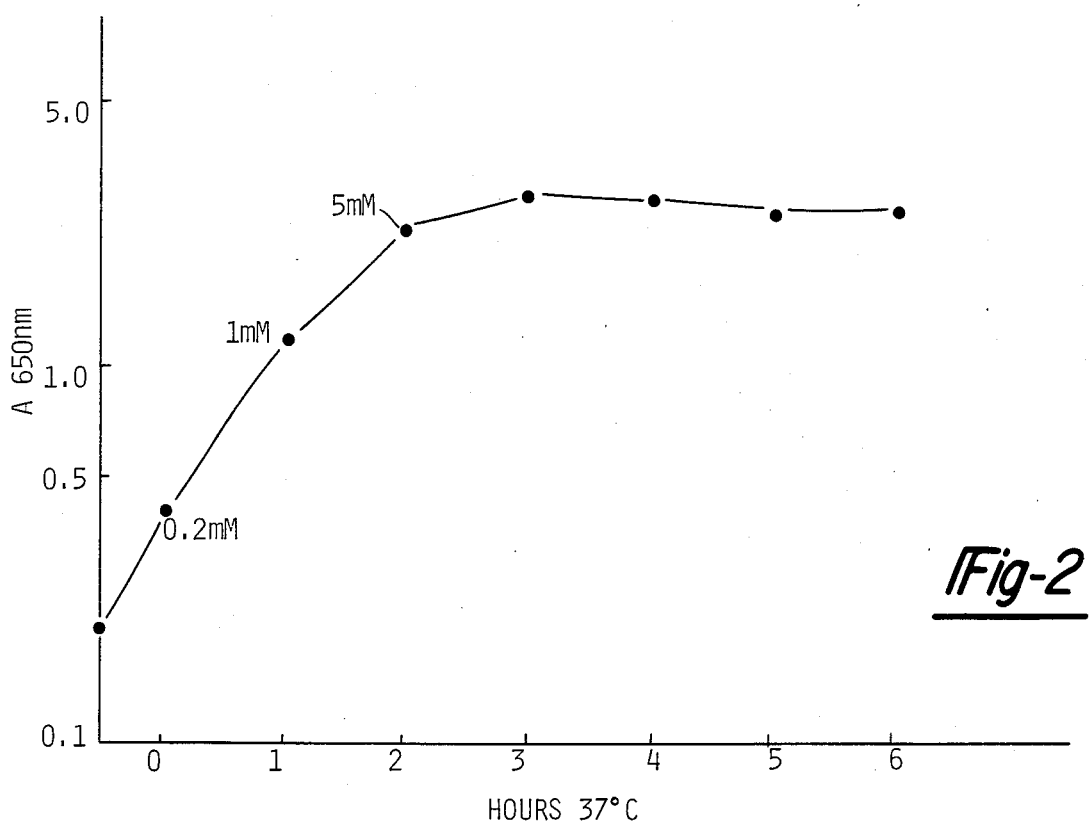

1.3. An attempt is then made to induce resistance to arsenite in *Bacillus subtilis* 168. An overnight culture is diluted twenty-fold in fresh medium. As soon as the growth is exponential, sodium arsenite is added at a final concentration of 0.2 mM (time 0 of the experiment). After one hour of incubation, the concentration of arsenite is raised to 1 mM, and one hour later to 5 mM. The growth at 37° C. with aeration is determined by measuring the absorbance at 650 nm. The results obtained are shown in FIG. 2.

The low concentrations are without significant immediate effect, whereas the strongest concentration of arsenite has an immediate inhibitory effect. It may be concluded that resistance to arsenite in this strain is not inducible. Inducibility of the resistance system was demonstrated in a strain of *Staphylococcus aureus* carrying a plasmid which brought about resistance to arsenic (4). After this result, the concentration of 5 mM was adopted for selecting the transformed cells.

1.4. The protoplasts are prepared and transformed as described. Dishes containing sodium arsenite on which untransformed protoplasts are plated remain sterile, while protoplasts treated with plasmid DNA give rise to colonies on this same medium. About a hundred colonies were withdrawn from different dishes and set up again in culture in liquid medium in the presence of 6 mM sodium arsenite. Fifteen clones produced relatively good growth again, and only one regularly gives rise to a culture similar to the untransformed strain cultured without arsenite. This strain, named *Bacillus subtilis* 44, has been studied in greater detail. The growth of the transformed strain 44 of *Bacillus subtilis* is studied in the presence of sodium arsenite. Culture of the transformed strain is carried out overnight in the presence of 5 mM sodium arsenite. This culture is then diluted twenty-fold in fresh medium, and for each subculture the concentration of arsenite is adjusted as shown on the curves. These cultures are incubated at 37° C. with agitation, and their evolution is followed by measuring the absorbance at 650 nm.

Figure 3:
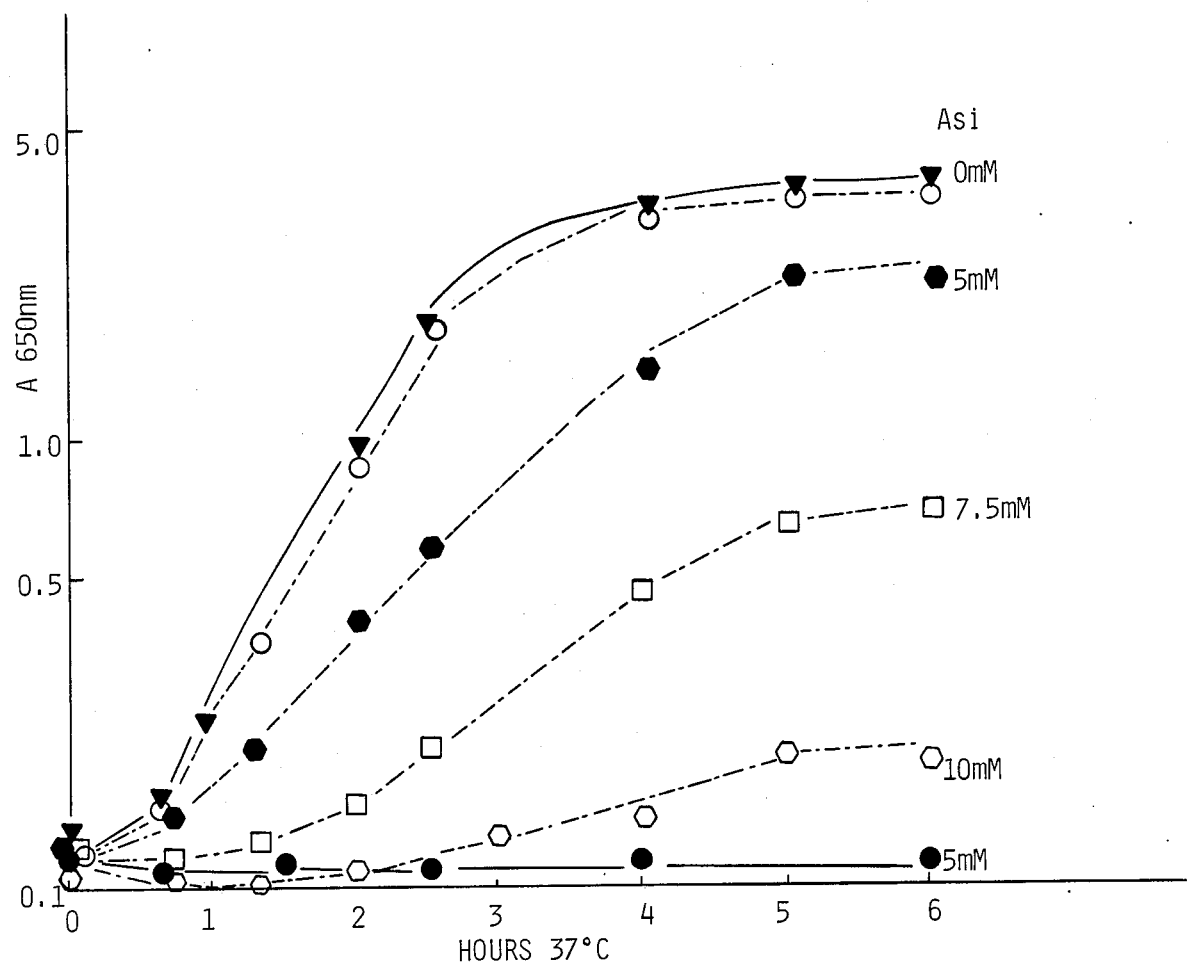

The curves in FIG. 3 show the trends in the growth of this strain in the presence of various concentrations of sodium arsenite. The transformed cells clearly withstand a concentration of 5 mM of inhibitor, whereas the original strain is completely inhibited under the same conditions. Higher concentrations of inhibitor are injurious to strain 44.

EXAMPLE 2

Transformation of *Thiobacillus ferrooxidans*

In the strain Tf35 a single plasmid of $13.5 \times 10^6$d was found. It was called pBP-1. The plasmid was separated by the methods described above.

This plasmid was nick-translated with $^{32}P$ according to the usual procedures, and radioactivity of $0.44 \times 10^6$ cmp/μg of DNA was obtained. The radioactive plasmid thus obtained was encapsulated in liposomes according to the method of Sene and Nicolau (9). 10 μM phosphatidyl ethanolamine (Sigma) and 3M egg phosphatidyl glycerol were dissolved in chloroform and evaporated under nitrogen in a rotary evaporator. The lipids were then dissolved in 1.5 ml of distilled ethyl ether. The ether solution was injected slowly into an aqueous solution of plasmid pBP-1 at 2 μg/ml in PBS (phosphate buffer—0.145M NaCl) at pH 7.4 heated to 60° C.

Nitrogen was bubbled for 15 minutes through the liposome suspension thereby obtained, in order to remove the ether residues present. In order to separate the plasmid encapsulated in the liposomes from the free plasmid, the suspension was incubated for 30 minutes at 37° C. with a solution of DNase I in the presence of 10 mM $MgCl_2$. The suspension was then chromatographed on a column of Sepharose 4B, and the liposomes containing the DNA were separated from the hydrolyzed DNA. 1.1 μg of plasmid were encapsulated in the liposomes (≃9% of the DNA present in solution).

The Tf35 protoplasts were prepared by modification of the method of Chang and Cohen (10). The protoplasts were regenerated by a method of culturing on silica gel impregnated with the inorganic salts necessary for growth:

| | |
|---|---|
| $MgSO_4.7H_2O$ | 0.4 g/liter |
| $K_2HPO_4$ | 0.4 g/liter |
| $(NH_4)_2SO_4$ | 0.4 g/liter |
| $Fe_2(SO_4)_3.7H_2O$ | 33.3 g/liter |

This method enables the protoplasts to be regenerated before being set up again in culture in liquid medium.

The protoplasts obtained from Tf35 in semilogarithmic phase ($OD_{44}=0.25$) cultured in Kelly-Tuovinen medium (7) were incubated for 1 hour at 34° C. with the liposomes containing plasmid pBP-1. After incubation, the liposome/protoplast suspension was centrifuged at 2600 g for 10 minutes.

The protoplasts were washed on several occasions (3 times) with Kelly-Tuovinen medium (7), and an aliquot was withdrawn and its radioactivity counted. According to the radioactive count, the protoplasts appeared to have incorporated ≃0.8–1.0% of the plasmid encapsulated in the liposomes.

The protoplasts were regenerated in the presence of 2.5 mM sodium arsenite. The capacity of these regenerated bacteria for oxidizing $Fe^{2+}$ was then measured and compared with that of the Tf35 controls and also with a strain of *Thiobacillus ferrooxidans* devoid of plasmid, Tf29. The results are given in Table I.

TABLE I

| Strain | Na arsenite mg/liter | $Fe^{2+}$ oxidized to $Fe^{3+}$ in 40 hours* (%) |
|---|---|---|
| Tf29 | 500 | 0 |
| (without plasmid) | 2500 | 0 |
| Tf35 | 500 | 10 |
| | 2500 | 4 |
| Tf35 | 500 | 20 |
| | 2500 | 17 |
| (enriched with plasmid by interaction with liposomes) | 0 | 22 |

*Initial concentration of $Fe^{2+} = 6.15$ g/liter

While the capacity of oxidizing $Fe^{2+}$ by Tf without plasmids or strain Tf35 is either completely or severely inhibited by Na arsenite, the bacterium TF 35 enriched with plasmid is much less inhibited by the same concentrations of Na arsenite.

The medium containing the arsenite acts as a selective medium for the "enriched" bacteria.

In this manner, bacteria sensitive to As(III)/As(V)—the vast majority of strains of *Thiobacillus ferrooxidans*—can, by acquiring a high resistance to arsenite/arsenate, be used for leaching deposits containing arsenopyrites.

The following strains of *Thiobacillus ferrooxidans* have been deposited at C.N.C.M., Institut Pasteur, Paris, on March 28, 1984 whereby the corresponding Accession No. is mentioned in parenthesis:

Tf29 (I—290)
Tf33 (I—291)
Tf35 (I—292)
Tf80 (I—293)

BIBLIOGRAPHY

1. Bosecker, K. and Kursten, M., Process Biochemistry, Oct. 1978, 2–4
2. Mao, M. W. H., Dugan, P. R., Martin, P. A. W. and Tuovinen, O. H., FEMS Microbiol. Letters 1980, 8, 121–125.
3. Martin, P. A. W., Dugan, P. R. and Tuovinen, O. H., Can. J. Microbiol. 1981, 27, 850–853.
4. Silver, S., Budd, K., Leahy, M., Shaw, W. V., Hammond, D., Novick, R. P., Willsky, G. R. Malamy, M. H. and Rosenberg, H., J. Bacteriol. 1981, 146, 983–996.
5. Curtin, M. E., Biotechnology, May, 1983, 229–235.
6. Maniatis, T., Fritsch, E. F. and Sambrook, J., Molecular cloning (A Laboratory Manual) C.H.S. Laboratory, 1982.
7. Tuovinen, O. H. and Kelly, D. P. Arch. Microbiol. 1973, 88, 285–298.
8. Chang, S. and Cohen, S. N., Molec. Gen. Genet. 1979, 168, 111–115.
9. Sene, C. and Nicolau, C. in "Liposomes, Drugs and Immunocompetent Cell Functions", Academic Press, London 1981, pp. 67–79.
10. Chang, T. and Cohen, P., 1979, Molec. Cell. Genetics 168, 111–115.

I claim:

1. A process for increasing the resistance of a bacterial strain to As(III) and As(V), comprising transforming a first bacterial strain selected from a group of transformable bacterial strains, said group consisting of *Thiobacillus ferrooxidans* and *Bacillus subtilis* by a plasmid carrying resistance to As(III) and As(V) which is capable of expression of said resistance in said first strain.

2. A process according to claim 1, wherein said plasmid is extracted from a second bacterial strain having resistance to As(III) and As(V).

3. A process according to claim 2, wherein said transforming comprises incubation of a protoplast of said first strain with a liposome incorporating said plasmid of said second strain.

4. A process according to claim 1, wherein said transformation comprises incubation of a protoplast of said first strain with a liposome incorporating said plasmid.

5. A process according to claim 4, wherein said first strain is *Thiobacillus ferrooxidans*.

6. A process according to claim 2, wherein said second strain is *Thiobacillus ferrooxidans*.

* * * * *